(12) United States Patent
Pan

(10) Patent No.: US 7,220,236 B2
(45) Date of Patent: May 22, 2007

(54) METHOD FOR ELIMINATING HIV IN HUMAN BLOOD AND A DEVICE FOR TREATING AIDS WITH NON-PHARMACOTHERAPY

(75) Inventor: Gang Pan, Beijing (CN)

(73) Assignee: Research Center for Eco-Environmental Sciences, The Chinese Academy of Sciences, Beijing (CN)

( * ) Notice: Subject to any disclaimer, the term of this patent is extended or adjusted under 35 U.S.C. 154(b) by 466 days.

(21) Appl. No.: 10/497,792

(22) PCT Filed: Jul. 19, 2002

(86) PCT No.: PCT/CN02/00507

§ 371 (c)(1),
(2), (4) Date: Jul. 22, 2004

(87) PCT Pub. No.: WO03/049788

PCT Pub. Date: Jul. 19, 2002

(65) Prior Publication Data

US 2005/0043666 A1 Feb. 24, 2005

(30) Foreign Application Priority Data

Dec. 10, 2001 (CN) .................. 01 1 40495
Jun. 28, 2002 (CN) .................. 02 1 24487

(51) Int. Cl.
*A61M 37/00* (2006.01)
*A61M 1/00* (2006.01)

(52) U.S. Cl. .................. 604/4.01; 604/6.11; 604/6.14; 604/5.01; 604/5.02; 422/44; 422/45

(58) Field of Classification Search .............. 604/6.11, 604/5.01, 5.02, 6.14, 4.01; 424/501, 422, 424/426; 514/885, 816, 817; 422/44, 1, 422/4, 45
See application file for complete search history.

(56) References Cited

U.S. PATENT DOCUMENTS 5,116,307 A  5/1992  Collins
5,419,759 A  5/1995  Naficy
5,484,396 A  1/1996  Naficy

FOREIGN PATENT DOCUMENTS

CN  01140495.7  12/2001
CN  02124487.1  6/2002

*Primary Examiner*—Jacqueline F. Stephens
(74) *Attorney, Agent, or Firm*—Milde & Hoffberg, LLP

(57) ABSTRACT

The invention provides a method for eliminating HIV in human blood and a device for treating AIDS with non-pharmacotherapy. The method includes (1) pumping the blood containing HIV virus into a soft thin plastic tube while adding air through a T-tube at a definite frequency so that the blood is evenly divided into very small blood droplets (2) introducing the small blood droplets into a screw-shaped quartz tube and exposing the quartz tube under a definite dosage of radiation to kill the HIV virus in the blood droplets is (3) collecting the treated blood in a storage bottle. Results show that after the HIV infected blood is divided into very small blood droplets and is irradiated with a definite dosage of ultraviolet (253.7 nm) for 90 seconds, more than 92% HIV loads in the blood is eliminated, while the lymphocyte (CD4+), erythrocyte, leucocyte and haemoglobin remain almost unchanged.

12 Claims, 8 Drawing Sheets

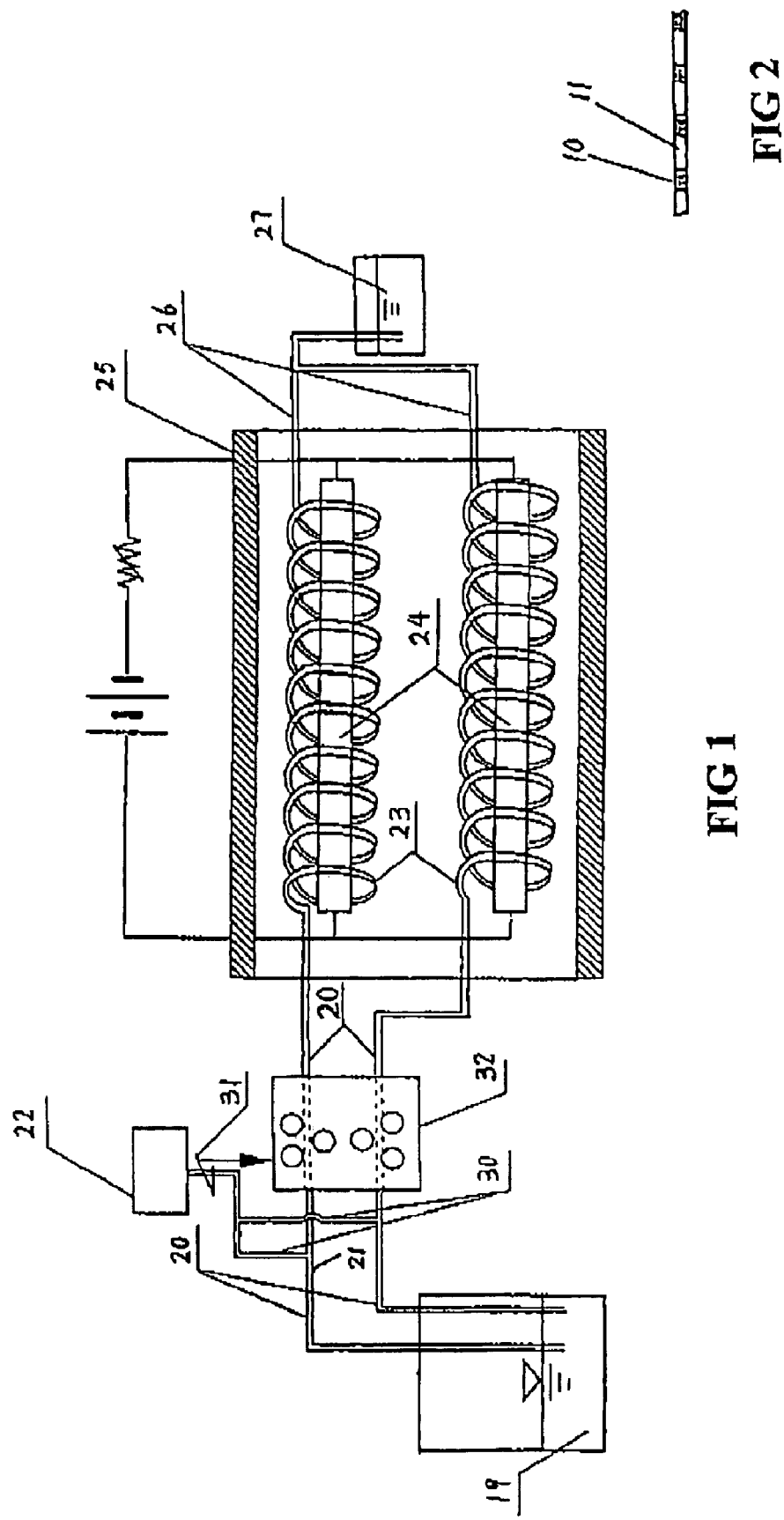

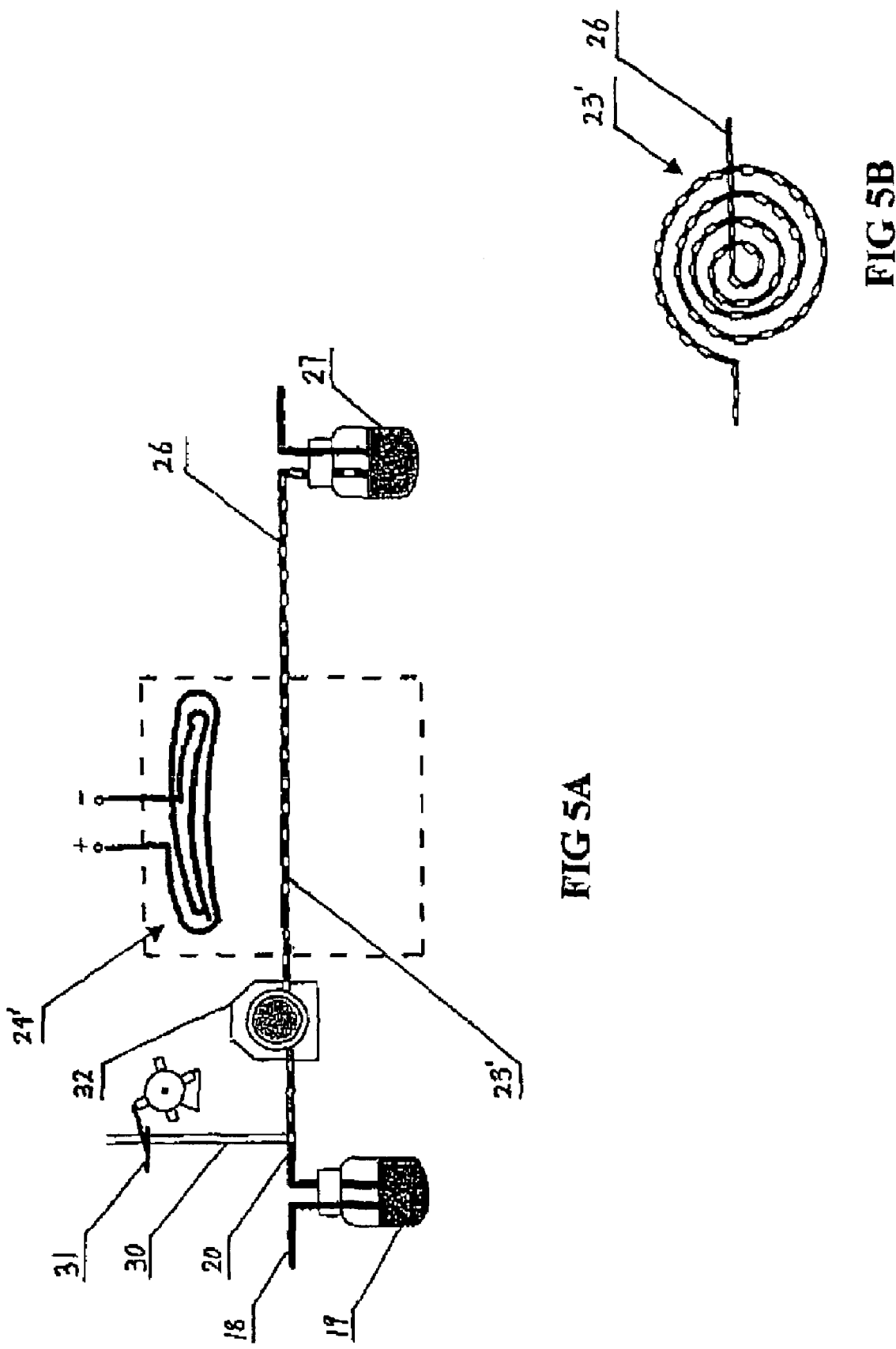

Figure 3:
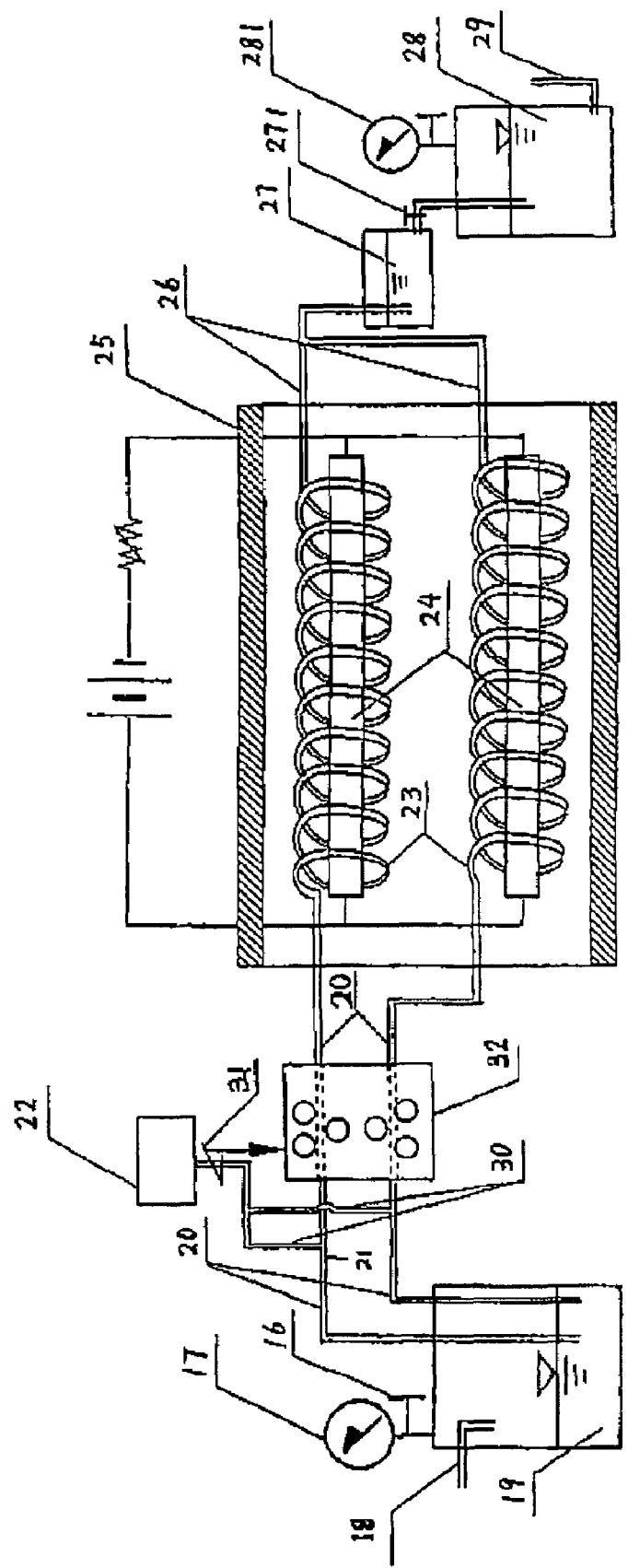

METHOD FOR ELIMINATING HIV IN HUMAN BLOOD AND A DEVICE FOR TREATING AIDS WITH NON-PHARMACOTHERAPY

TECHNICAL FIELD

This invention relates to a method for eliminating HIV in human blood and a device for treating AIDS with non-pharmacotherapy.

BACKGROUND ART

There has been no therapy in the world so far to cure AIDS radically. The conventional therapies are mainly to lower the level of HIV or restrain the replication of HIV virus in human bodies using medicines (pharmacotherapy). These therapies, such as the "cocktail" therapy, have insurmountable problems of strong side effects and drug-resistance, although their curative effect is improving rapidly. The medicines commonly used for AIDS treatment can cause nausea, headache, anemia, decrease in neutrophil leucocyte, pancreatic inflammation and acid toxicosis, and sometimes peripheral neuropathy, diabetes, hepatitis and alimentary canal symptoms. Moreover, as these therapies are usually expensive, they can hardly be effective to the large population of AIDS patients with ordinary incomes in many countries.

In recent years, ideas of extracorporeal blood treatment have been brought forward, as described in the American Patents, Nos. 272535, 068510 and 549961. This method is to take a certain amount of blood from an AIDS patient, treat it with volatile organic solvent diethyl ether to kill the dissociative or intracellular HIV, and then transfuse the treated blood back to the patient. In this method organic solvent is mixed with human blood, which may inevitably impose side effects on the normal cells in the blood, though the solvent can volatilize from the blood eventually. Furthermore, this method involves chemical treatment to blood and a series of complicated operations, leaving a lot to work on for practical application.

DISCLOSURE OF THE INVENTION

The aim of this invention is to provide a method of non-pharmacotherapy for eliminating HIV in human blood, which possesses such characteristics as selective elimination of HIV in human blood without using any drugs or chemical reagents, safe and easy operation, and cost effective compared with the conventional pharmacotherapy.

Another aim of this invention is to provide a device for treating AIDS with non-pharmacotherapy, which possesses such characteristics as selective elimination of HIV in human blood without using any drugs or chemical reagents, safe and easy operation, and cost effective compared with the conventional pharmacotherapy. This device enables AIDS patients to receive extracorporeal circulative treatment at any moment till most HIV viruses are eliminated from their bodies, and keeps the treatment cost much lower than that of the conventional pharmacotherapy, making it possible for the large population of AIDS patients with low income to receive effective treatment.

To achieve the above-mentioned aims, the invention provides a method for eliminating HIV in human blood, which possesses characteristics and includes steps as below:

(1) pumping the blood containing HIV virus into a soft thin plastic tube while simultaneously adding air bubbles through a T-tube at a definite frequency so that the blood is evenly divided into very small blood droplets by the air within the plastic tube after the T-tube;

(2) introducing the small blood droplets into a screw-shaped quartz tube and exposing the quartz tube under a definite dosage of radiation so that the HIV virus in the blood droplets is selectively killed by the radiation;

(3) collecting the treated blood in a storage bottle.

The invention can have extended technical characteristics as below:

(1) The screw tube can be shaped into a disc to become a disc-shaped screw quartz tube, above which a disc-shaped ultraviolet lamp is set.

(2) The middle part of the soft plastic tube, which is connected to a gas source via a gas transporting tube, is clipped in the channel of a multi-channel wiggle pump.

(3) An off-and-on clamp is set on the gas transporting pipe to control the gas flow to on or off mode. The clamp includes a movable upper splint and a fixed lower splint, jointed together with a pivot. The gas transporting pipe passes through the clamp between the splints. A pinchcock is set around the pivot to the splints, and a rotational cam is set to bunt the upper splint at the open end.

(4) The gas source can be a gas chamber, in which disinfected air or virus-killing volatile gas is stored.

The characteristics of the said method for eliminating HIV in blood are that the said method adopts extracorporeal circulative treatment to kill HIV, that a storage bottle for receiving virus infected blood is connected to a soft plastic tube and to the patient via an exsanguinating pipe, and that a storage bottle for collecting healthy blood is connected to a transfusion bottle, which is connected to the patient via a blood transfusion device.

The characteristics of the said device for treating AIDS with non-pharmacotherapy are that it includes al least one soft plastic tube connecting to a storage bottle for virus infected blood, with its middle part clipped in the channel of a multi-channel wriggle pump and is connected to a gas source via a gas transporting pipe controlled by a clamp, and that a screw tube beside a radiant point is connected to the outlet of the soft plastic tube and to a storage bottle for healthy blood via a blood transfusion pipe.

The said device for treating AIDS with non-pharmacotherapy can also possess extended technical characteristics as below:

(1) The screw tube can be a screw quartz tube, set in a thermostat. The radiant point is an ultraviolet point.

(2) The screw tube can be a disc-shaped screw quartz tube, and the radiant point is a disc-shaped ultraviolet lamp. The disc-shaped screw quartz tube is set under the disc-shaped ultraviolet lamp.

(3) The screw tube can be an orbicular screw quartz tube, and the radiant point is a cannular ultraviolet lamp. The orbicular screw quartz tube is set around the cannular ultraviolet lamp.

(4) The clamp controlling the gas flow mode includes a movable upper splint and a fixed lower splint, jointed together with a pivot. The gas transporting pipe passes through the clamp between the splints. A pinchcock is set around the pivot to the splints, and a rotational cam is set to bunt the upper splint at the open end.

(5) The gas source can be a gas chamber, in which disinfected air or virus-killing volatile gas is stored.

(6) The storage bottle for virus infected blood is connected to the patient via an exsanguinating pipe, and the storage bottle for healthy blood is connected to a transfusion bottle, which is connected to the patient via a blood transfusion device.

The said method for eliminating HIV in blood makes it possible to let the blood from patients be exsanguinated into a screw quartz tube in a closed extracorporeal circulative device, where HIV viruses in the blood were killed and the treated blood transfused back to the patient. The HIV infected blood is first divided into many very small blood droplets by a virus-killing volatile gas (medicine). As the medicine can kill the virus more effectively in very small blood droplets, its pharmic effect can be greatly promoted. Then the small blood droplets are exposed to the radiant point (ultraviolet), which can function on the small blood droplets fully and kill the virus inside effectively. Experimental results showed that a definite dosage of irradiation (UVC) eliminated most of the HIV in the small blood droplets without causing significant damage to the basic components of the blood such as lymphocyte, red blood cell (erythrocyte), white blood cell (leucocyte) and haemoglobin. The invention therefore possesses such characteristics as selective elimination of HIV in human blood, safe and easy operation, and cost effective compared with the conventional pharmacotherapy.

The said device for treating AIDS with non-pharmacotherapy makes it possible to: firstly, let blood from one arm of the AIDS patient and divide it into many very small blood droplets; secondly, irradiate the blood droplets effectively with UVC so that the radiation can penetrate the blood droplet; and finally, transfuse the treated blood back to the other arm of the patient, completing the closed extracorporeal circulative treatment. The said operation is safe and convenient, and generally involves no chemical reagents or drugs; therefore there are no problems of drug resistance, poisonous and other chemical side effects. In addition, the device possesses characteristics derived from the closed extracorporeal circulative treatment such as selective elimination of HIV in human blood, safe and cost effective, which enables the patient to be treated at any moment with repeated operations of the extracorporeal circulative treatment. The cost of this method is much lower than that of the conventional pharmacotherapy, such as the "cocktail" therapy, making it possible for the patients with low income to receive effective AIDS treatment.

The experimental results show that within a suitable dosage of irradiation (ultraviolet-C) the HIV in the small blood droplets can be killed selectively, while imposing little damage to the basic components of the blood, such as lymphocyte, red blood cell (erythrocyte), white blood cell (leucocyte) and haemoglobin. The results show that after the blood from the AIDS patient is divided into small blood droplets through the said device and is irradiated with the ultraviolet (253.7 nm) at 4300 mW/cm2 for 90 seconds, the HIV loads in blood decrease 92%, while the level of lymphocyte (CD4+), erythrocyte, leucocyte and haemoglobin remain almost the same.

DESCRIPTION OF FIGURES

FIG. 1. Schematic illustration of the method in the said invention for eliminating HIV in blood.

FIG. 2. Schematic illustration of the effect to divide the HIV infected blood into very small blood droplets in a quartz tube.

FIG. 3. Schematic illustration of the device for treating AIDS with non-pharmacotherapy as an optimal set-up of this invention.

FIG. 4. Schematic illustration of the off-and-on clamp controlling the gas flow as marked in FIG. 3.

FIG. 5A. Schematic illustration of the disc-shaped screw quartz tube and the matching disc-shaped ultraviolet lamp of said device.

FIG. 5B. Planform of the disc-shaped screw quartz tube in FIG. 5A.

FIGS. 6A-6G. Experimental results obtained using the said device. FIG. 6A: Change of HIV loads after the treatment of the method as compared with lymphocyte CD4+ in Case 1. FIG. 6B: Change of HIV loads after the treatment as compared with lymphocyte CD4+ in Case 2. FIG. 6C: Change of lymphocyte in Cases 3, 4 and 5 after the treatment. FIG. 6D: Change of haemoglobin in Cases 3, 4 and 5 after the treatment. FIG. 6E: Change of the average volume of erythrocyte in Cases 3, 4 and 5 after the treatment. FIG. 6F: Change of leucocyte in Cases 3, 4 and 5 after the treatment. FIG. 6G: Change of erythrocyte in Cases 3, 4 and 5 after the treatment.

DETAILED DESCRIPTION OF THE EMBODIMENTS

Referring to FIG. 1, the said method for eliminating HIV in human blood includes the following steps:

(1) Pumping the blood containing HIV into a soft plastic tube 20 with its middle part 21 connected to a gas chamber 22 via a gas transporting pipe 30, in which disinfected air or virus-killing volatile gas, such as the volatile organic solvent diethyl ether, is stored. An off-and-on clamp 31 is set on the gas transporting pipe 30, which can control the gas flow from the gas chamber 22 to the soft plastic tube 20 by clamping (off mode) and loosening (on mode) at a definite frequency, and therefore divide the blood in the soft plastic tube 20 into small blood droplets 10 as shown in FIG. 2. Every small blood drop 10 is isolated by the gas bubble 11, so that the irradiation (ultraviolet) can function fully on the small blood droplets 10 and kill the virus inside effectively. The middle part of the soft plastic tube 20 is clipped in the channel of a multi-channel wriggle pump 32, which provides the driving force for one-way movement of the blood and insufflation of the gas into the soft plastic tube 20 from the gas chamber 22.

(2) The outlet of the soft plastic tube 20 is connected to a screw quartz tube 23. Irradiation from an ultraviolet radiant point 24 can kill the virus in the small blood droplets 10 when they pass through the screw quartz tube 23. The screw quartz tube 23 can be a disc-shaped quartz tube 23' (FIG. 5B), and the radiant point 24 can be a disc-shaped ultraviolet lamp 24' (FIG. 5A). The disc-shaped quartz tube 23' is set under the disc-shaped ultraviolet lamp 24' as shown in FIGS. 5A and 5B. The limit and speed to kill the HIV in blood by ultraviolet irradiation can be controlled through adjusting the radiant intensity of the ultraviolet lamp, the temperature of the thermostat and the exposure time of the discrete blood droplets to the irradiation.

(3) Infuse the treated blood in the bottle to collect the treated blood 27.

The said off-and-on clamp 31 can be designed in different forms, which is not a difficult job for technicians in this field. One practical design is shown in FIG. 4. The clamp includes a movable upper splint 311 and a fixed lower splint 312, jointed together with a pivot 313. The gas transporting pipe 30 passes through the clamp between the splints. A pinchcock 314 is set around the pivot to the splints, which can engage the splints and prevent the gas from passing through. A rotational cam 315 is set under the open end of the upper splint 311 to bunt the upper splint at a definite frequency, which can allow the gas to pass through. The frequency of clamping (off mode) and loosening (on mode) of the gas transporting pipe 30 by the clamp 31 is controlled by the rev of the rotational cam 315.

The said method for eliminating HIV in blood in this invention adopts extracorporeal circulative treatment to kill HIV. As shown in FIG. 3, a storage bottle for receiving virus infected blood 19 is connected to a soft plastic tube 20 and to the patient via an exsanguinating pipe 18. A storage bottle for collecting healthy blood 27 is connected to a transfusion bottle 28, which is connected to the patient via a blood transfusion pipe 29.

Referring to FIG. 3, the said device for treating AIDS with non-pharmacotherapy includes two soft plastic tubes 20. The soft plastic tubes 20 are connected to the bottle for receiving virus infected blood 19, which is connected to one arm of the patient via an exsanguinating pipe 18. First, let the HIV infected blood from one arm of the patient to the storage bottle 19 via the exsanguinating pipe 18 using a decompression pump 17, and then set the pressure in the storage bottle 19 as normal by adjusting the valve 16. Transport the virus infected blood to several soft plastic tubes 20 (only two are shown in the figure) using the multi-channel wriggle pump 32. The middle parts of the soft plastic tubes 20 are clipped in the channels of the multi-channel wriggle pump 32, and are connected to the gas chamber 22 via the gas transporting pipes 30. A off-and-on clamp 31 is set on the gas transporting pipe 30, which controls the gas transportation by clamping (off mode) and loosening (on mode) at a definite frequency. The movement of the clamp can be driven by the motor in the multi-channel wriggle pump 32 via a transmission device (not shown in the figure), insufflating the gas from the gas chamber 22 to the soft plastic tubes 20. The gas from the gas chamber 22 is insufflated at a definite frequency into the soft plastic tubes 20, dividing the blood into small blood droplets as shown in FIG. 2. Every small blood drop 10 is isolated by gas bubble 11, so that the irradiation (ultraviolet) can function fully on the small blood droplets 10 and kill the virus inside effectively. The gas chamber 22 is used to store disinfected air, or other volatile virus-killing gases (e.g. volatile organic solvent diethyl ether or other medicine). The temperature of the gas chamber 22 is controllable. Driven by the multi-channel wriggle pump 32, the small blood droplets 10 enter the thin screw quartz tubes 23, and circulate at a stable speed around the ultraviolet radiant point (e.g. a cannular ultraviolet lamp) 24 surrounded by the soft plastic tubes 23. The ultraviolet radiant point 24 and the surrounding screw quartz tube 23 can have different shapes (e.g. circular or gyral) in order to control the distance and time of the movement of the small blood droplets in the thermostat 25. The radiant intensity of the ultraviolet radiant point is controllable. As shown in FIG. 3, the screw quartz tube 23 is an orbicular screw quartz tube, and the radiant point is a cannular ultraviolet lamp. The orbicular screw quartz tube is set around the cannular ultraviolet lamp.

Referring to FIGS. 5A and 5B, the screw quartz tube can be a disc-shaped screw quartz tube 23', and the radiant point can be a disc-shaped ultraviolet lamp 24'. The disc-shaped screw quartz tube 23' is set under the disc-shaped ultraviolet lamp 24'.

The limit and rate to kill the virus (e.g. HIV) in blood by ultraviolet irradiation can be promoted by controlling the processes of dividing the blood and adjusting the radiant intensity, the temperature and the exposure time to the irradiation. When the blood is divided into small blood droplets by the virus-killing volatile gas (medicine), the medicine can kill the virus effectively in every small blood drop, and hence promotes its pharmic effect greatly. The treated blood is transported to the storage bottle 27 via a blood transporting pipe 26, and to the transfusion bottle 28 through a control valve 271. The healthy blood can be transfused to the other arm of the patient by adjusting the baric pump 281 on the transfusion bottle 28.

Figure 4:
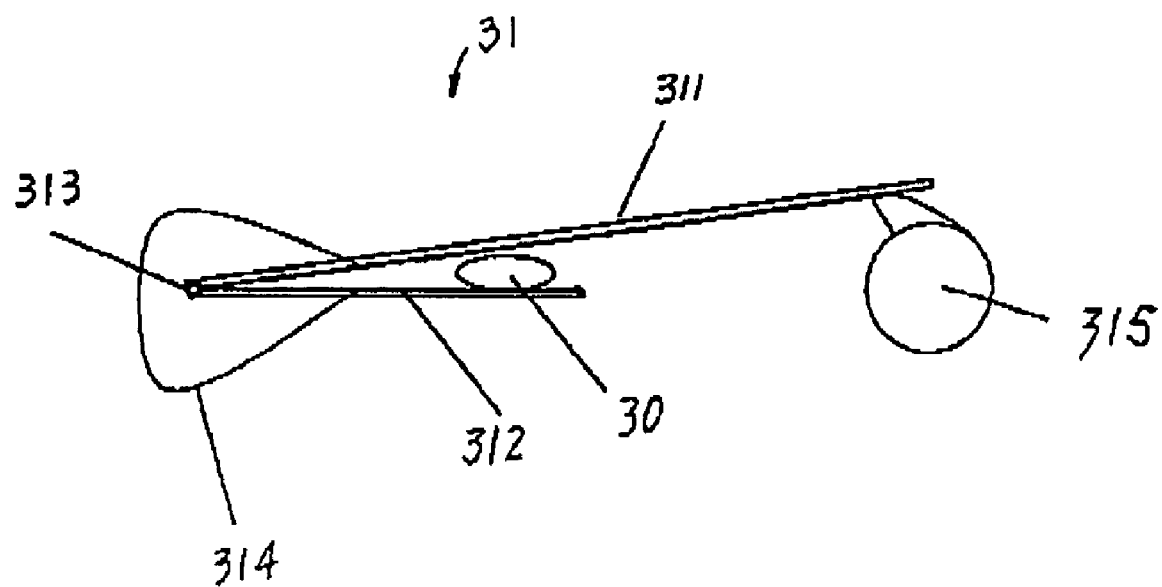

The said clamp controlling the gas input through the gas transporting pipe 30 by clamping and loosening at a definite frequency 31 can be designed in different forms, which is not a difficult job for technicians in this field. As shown in Figure 4, the clamp 31 includes a movable upper splint 311 and a fixed lower splint 312, jointed together with a pivot 313. The gas transporting pipe 30 passes through the clamp between the splints. A pinchcock 314 is set around the pivot to the splints, which can engage the splints and prevent the gas from passing through. A rotational cam 315 is set under the open end of the upper splint 311 to bunt the upper splint at a definite frequency, which can allow the gas to pass through. The frequency of clamping and loosening of the gas transporting pipe 30 by the clamp 31 is controlled by the rev of the rotational cam 315.

Figure 6A:
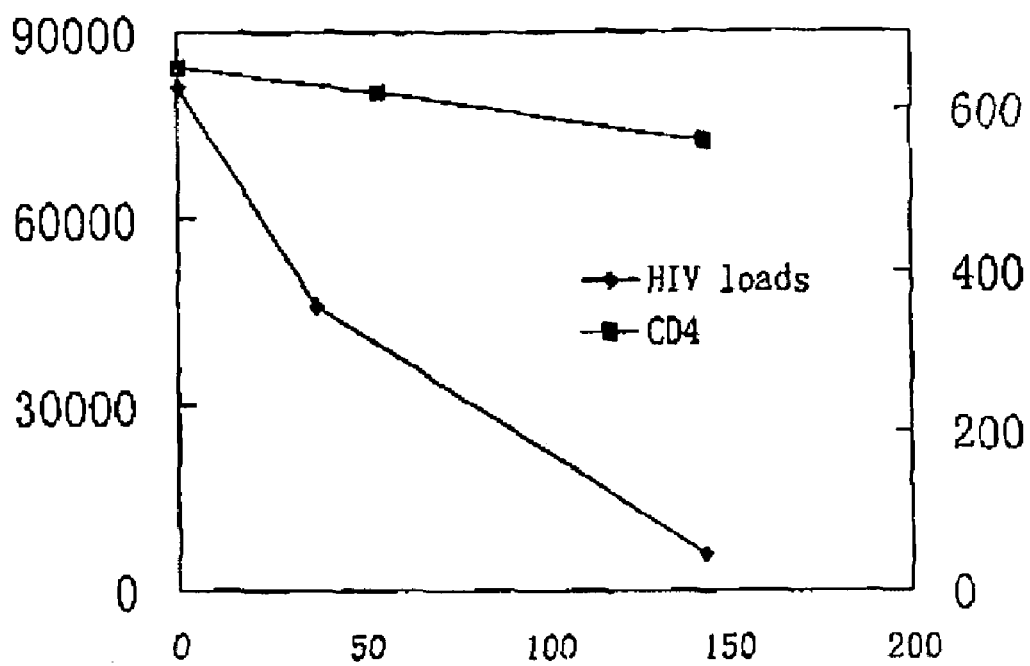
Figure 6B:
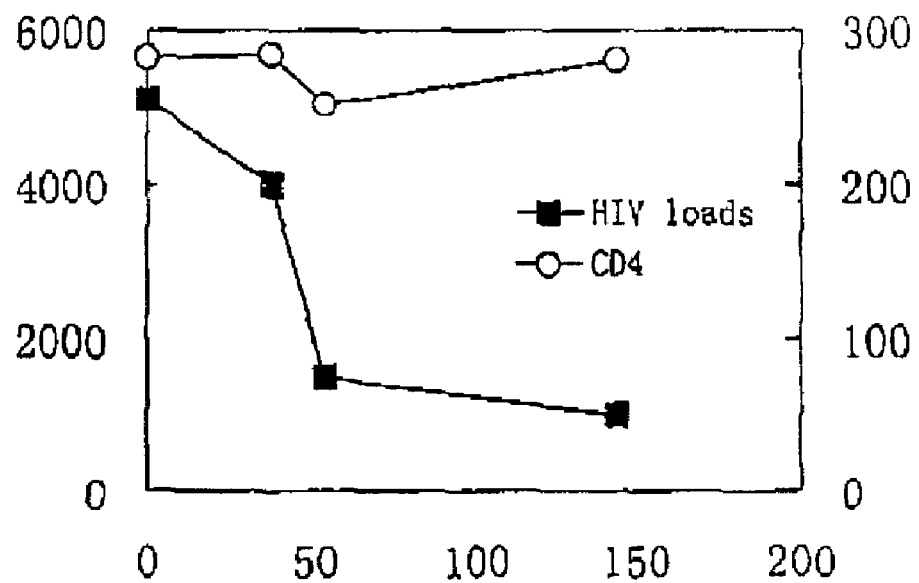
Figure 6C:
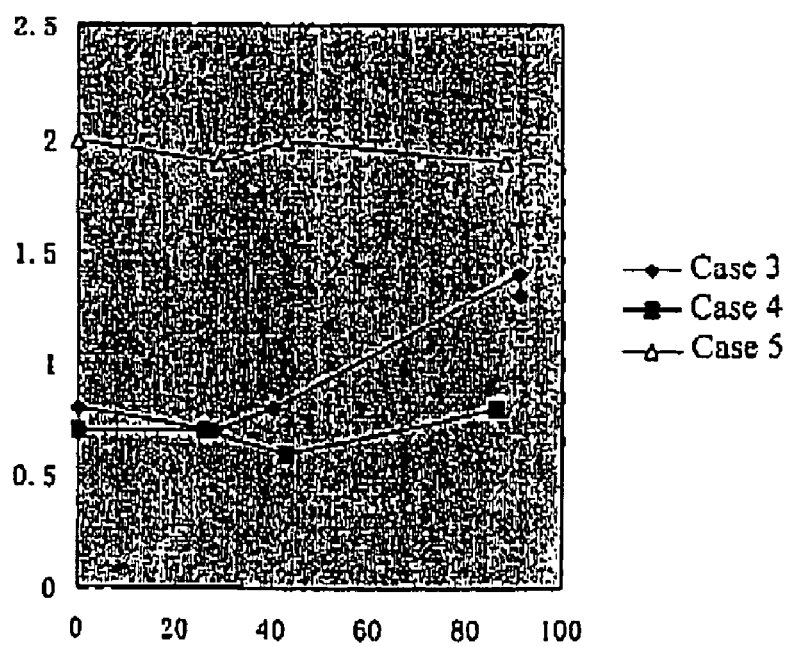
Figure 6D:
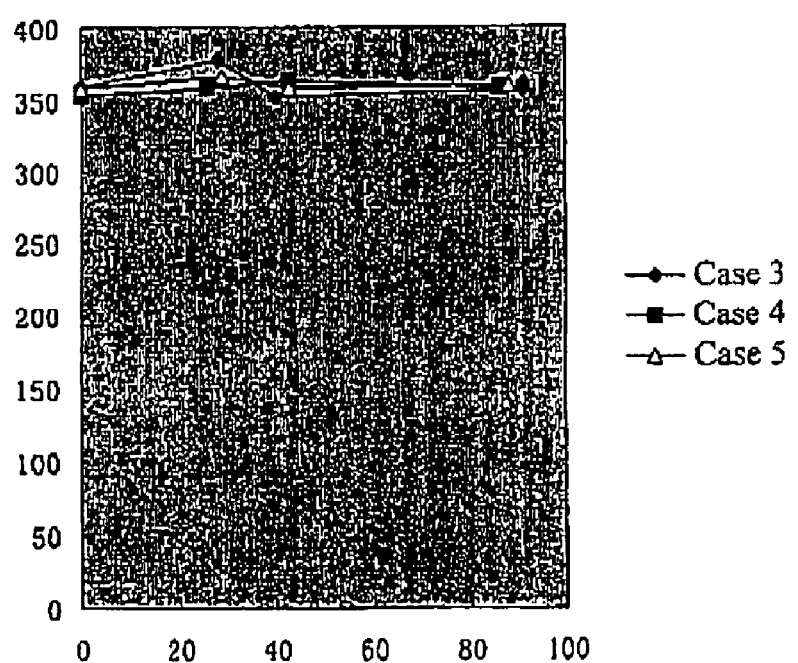
Figure 6E:
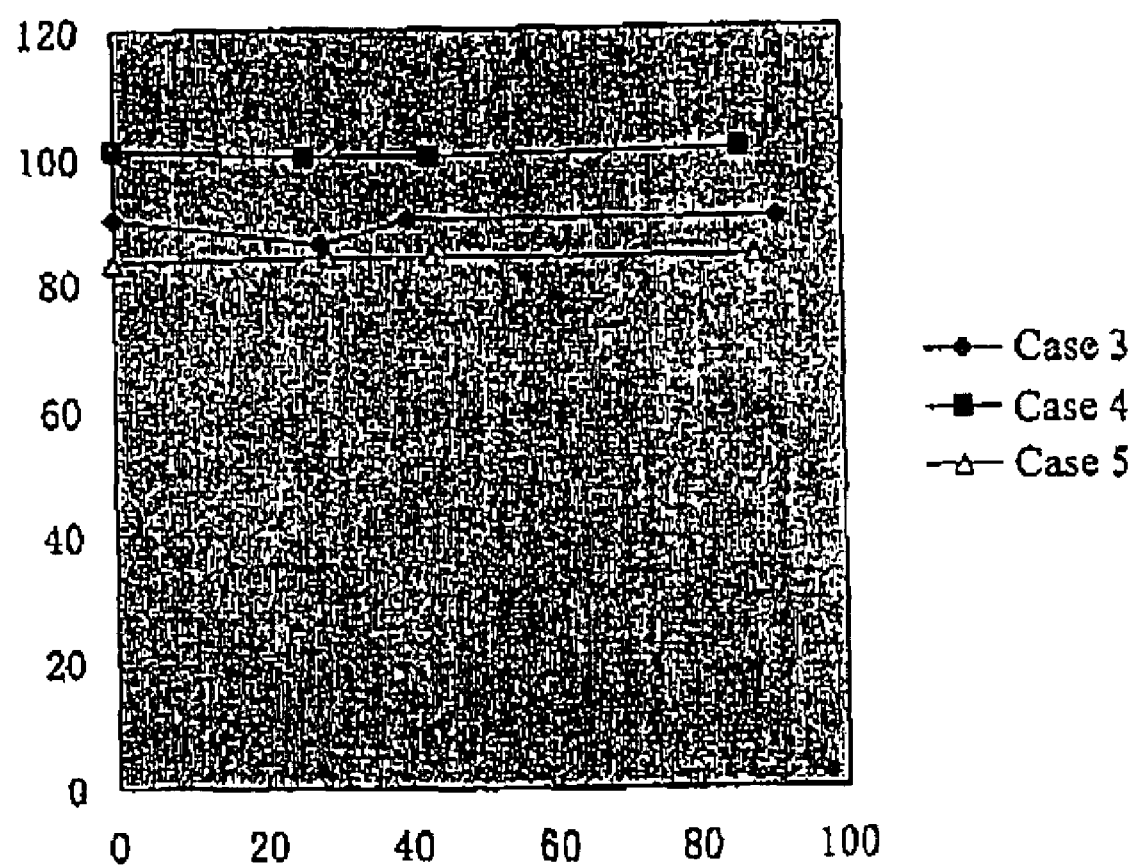
Figure 6F:
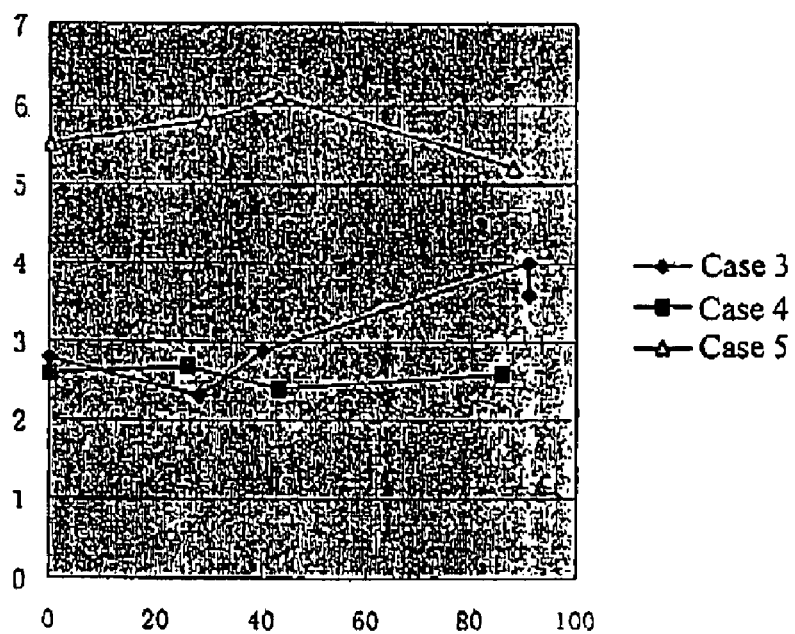
Figure 6G:
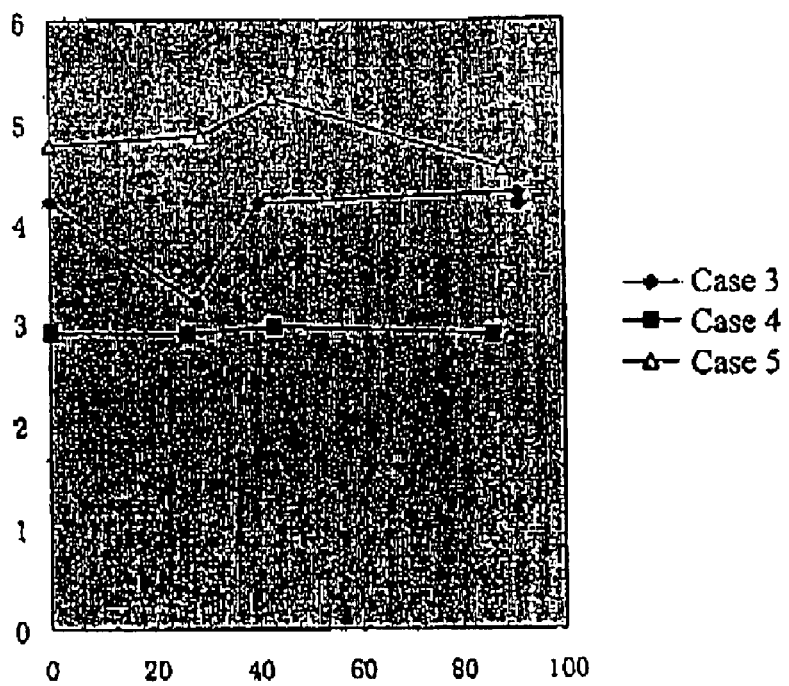

FIGS. 6A-6G show the results of virus-killing experiments at room temperature, using the said method for eliminating HIV in blood and the said device for treating AIDS with non-pharmacotherapy in this invention as shown in FIGS. 5A and 5B. The radiant intensity of the ultraviolet (253.7 nm) irradiation is 4300 mW/cm2. FIG. 6A shows the change of HIV loads after treatment as compared with lymphocyte CD4+ in Case 1, where the horizontal axis is irradiation time in seconds (s) and the vertical axis is HIV loads in (number)/ml. FIG. 6B shows the change of HIV loads as compared with lymphocyte CD4+ in Case 2, where the horizontal axis is irradiation time in seconds (s) and the vertical axis is HIV loads in (number)/ml. FIG. 6C shows the change of lymphocyte in Cases 3, 4 and 5 after the treatment, where the horizontal axis is irradiation time in seconds (s) and the vertical axis is the number of lymphocyte in 10E6/L. FIG. 6D shows the change of average haemoglobin in Cases 3, 4 and 5 after the treatment, where the horizontal axis is irradiation time in seconds (s) and the vertical axis is the average haemoglobin in g/L. FIG. 6E shows the change of average volume of erythrocyte in Cases 3, 4 and 5 after the treatment, where the horizontal axis is irradiation time in seconds (s) and the vertical axis is the average volume of erythrocyte in fL. FIG. 6F shows the change of leucocyte in Cases 3, 4 and 5 after the treatment, where the horizontal axis is irradiation time in seconds (s) and the vertical axis is the number of leucocyte in 10E9/L. FIG. 6G shows the change of erythrocyte in Cases 3, 4 and 5 after the treatment, where the horizontal axis is irradiation time in seconds (s) and the vertical axis is the number of erythrocyte in 10E12/L.

The results show that after the HIV infected blood is divided into very small blood droplets through the said device and is irradiated with the ultraviolet (253.7 nm) at 4300 mW/cm2 for 90 seconds, the HIV loads in blood of Cases 1 and 2 decrease 92%, while the lymphocyte (CD4+), erythrocyte, leucocyte and haemoglobin remain almost the same, as shown in FIGS. 6A-6G.

INDUSTRIAL APPLICABILITY

The said method and device provide new ideas, principles, and designs for the development of extracorporeal circulative treatment instruments to treat AIDS patients using non-pharmacotherapy, which allows the patients to be treated continuously and cost effectively from one arm to the other by the instrument without using drugs or chemicals. The said method and device also provide new ideas, principles, and designs for the development of new instruments to treat storage human blood for killing HIV and other viruses without using drugs or chemicals before it is used for the blood transfusion.

The invention claimed is:

1. A method for eliminating HIV in human blood comprising the steps of:
   (1) pumping the HIV infected blood into a soft plastic tube with its middle part connecting to a gas source, which supplies a gas bubble at a definite frequency into the tube so as to divide the blood in the tube into very small blood droplets;
   (2) introducing the small blood droplets into a thin quartz tube and irradiate the blood droplets to kill the virus inside the blood with a radiant point;
   (3) collecting the treated blood droplets with a storage bottle, which may be transfused back to the human patient.

2. The method for eliminating HIV in human blood defined in claim 1, wherein the quartz tube is a disc-shaped screw quartz tube, and the radiant point is a disc-shaped ultraviolet lamp, and wherein the disc-shaped screw quartz tube is set under the disc-shaped ultraviolet lamp.

3. The method for eliminating HIV in human blood defined in claim 2, wherein the middle part of the soft plastic tube is clipped into a multi-channel wriggle pump and is connected to a gas source via a gas transporting pipe, on which a clamp is set to control the flow of the gas to an on or off mode at a desired frequency.

4. The method for eliminating HIV in human blood in claim 3, wherein the clamp includes a movable upper splint and a fixed lower splint, joined together with a pivot; wherein the gas transporting pipe passes through the clamp between the splints; and wherein a pinchcock is set around the pivot to the splints, and a rotational cam is set to bunt the upper splint at the open end.

5. The method for eliminating HIV in human blood defined in claim 3, wherein the method adopts extracorporeal circulative treatment to kill HIV, wherein a storage bottle for receiving virus infected blood is connected to a soft plastic tube and to the patient via an exsanguinating pipe, and wherein a storage bottle for collecting treated blood is connected to a transfusion bottle, which is connected to the patient via a blood transfusion pipe.

6. The method for eliminating HIV in human blood defined in claim 1, wherein the gas source is a gas chamber, in which at least one of clean air and a virus-killing volatile gas is stored.

7. A device for treating AIDS with non-pharmacotherapy comprising, in combination: at least one soft plastic tube adapted for connection to a storage bottle for virus infected blood, having its middle part clipped into a multi-channel wriggle pump and connected to a gas source controlled by a clamp, and a thin quartz tube beside a radiant point adapted for connection through a soft plastic tube to a storage bottle for collecting treated blood.

8. The device for treating AIDS with non-pharmacotherapy defined in claim 7, wherein the thin quartz tube is a disk-shaped screw quartz tube, and the radiant point is a disk-shaped ultraviolet lamp, and wherein the screw quartz tube and the ultraviolet lamp are set in a thermostat.

9. The device for treating AIDS with non-pharmacotherapy defined in claim 7, wherein the quartz tube is an orbicular screw quartz tube, and the radiant point is a cannular ultraviolet lamp, and wherein the orbicular screw quartz tube is set around the cannular ultraviolet lamp.

10. The device for treating AIDS with non-pharmacotherapy in claim 7, wherein the clamp controlling the gas flow includes a movable upper splint and a fixed lower splint, jointed together with a pivot, wherein the gas transporting pipe passes through the clamp between the splints, and wherein a pinchcock is set around the pivot to the splints, and a rotational cam is set to bunt the upper splint at the open end.

11. The device for treating AIDS with non-pharmacotherapy defined in claim 10, wherein the gas source is a gas chamber, in which at least on of clean air and a virus-killing volatile gas is stored.

12. The device for treating AIDS with non-pharmacotherapy defined in claim 11, wherein the storage bottle for virus infected blood is connected to the patient via an exsanguinating pipe, and the storage bottle for treated blood is connected to a transfusion bottle, which is connected to the patient via a blood transfusion pipe.

* * * * *

UNITED STATES PATENT AND TRADEMARK OFFICE
CERTIFICATE OF CORRECTION

| | |
|---|---|
| PATENT NO. | : 7,220,236 B2 |
| APPLICATION NO. | : 10/497792 |
| DATED | : May 22, 2007 |
| INVENTOR(S) | : Gang Pan |

It is certified that error appears in the above-identified patent and that said Letters Patent is hereby corrected as shown below:

ON THE TITLE PAGE, LEFT COLUMN:

(87) should read as follows:

PCT PUBL DATE: JUN 19, 2003

Signed and Sealed this

First Day of July, 2008

JON W. DUDAS
*Director of the United States Patent and Trademark Office*